US012630693B2

(12) United States Patent
Schmidt et al.

(10) Patent No.: US 12,630,693 B2
(45) Date of Patent: May 19, 2026

(54) SMALL-CELL POLYSTYRENE FOAMS, AND PROCESS FOR PRODUCING SAME

(71) Applicant: INEOS STYROLUTION GROUP GMBH, Frankfurt am Main (DE)

(72) Inventors: Hans-Werner Schmidt, Bayreuth (DE); Klaus Kreger, Wiesau (DE); Bastian Klose, Gottmadingen (DE)

(73) Assignee: INEOS STYROLUTION GROUP GMBH, Frankfurt am Main (DE)

( * ) Notice: Subject to any disclaimer, the term of this patent is extended or adjusted under 35 U.S.C. 154(b) by 750 days.

(21) Appl. No.: 17/999,010

(22) PCT Filed: May 17, 2021

(86) PCT No.: PCT/EP2021/062951
§ 371 (c)(1),
(2) Date: Nov. 16, 2022

(87) PCT Pub. No.: WO2021/233811
PCT Pub. Date: Nov. 25, 2021

(65) Prior Publication Data
US 2023/0227627 A1 Jul. 20, 2023

(30) Foreign Application Priority Data
May 19, 2020 (EP) .................................... 20175406

(51) Int. Cl.
*C08J 9/12* (2006.01)
*C07C 233/43* (2006.01)
(Continued)

(52) U.S. Cl.
CPC .............. *C08K 5/20* (2013.01); *C07C 233/43* (2013.01); *C07C 233/62* (2013.01);
(Continued)

(58) Field of Classification Search
CPC ....... C08K 5/20; C07C 233/43; C07C 233/62; C07C 233/80; C07C 2601/14;
(Continued)

(56) References Cited

U.S. PATENT DOCUMENTS 5,210,105 A 5/1993 Paquet et al.
5,489,407 A 2/1996 Suh et al.
(Continued)

FOREIGN PATENT DOCUMENTS

CN 101796091 A 8/2010
CN 107075130 A 8/2017
(Continued)

OTHER PUBLICATIONS

M. Stumpf et al. in Journal of Cellular Plastics 2011, 47(6), 519-534.
(Continued)

*Primary Examiner* — K. Boyle
(74) *Attorney, Agent, or Firm* — RAPHAEL BELLUM PLLC

(57) ABSTRACT

The invention relates to a process for producing small-cell foams from a styrene-polymer component (S) and an additive of formula (I), wherein Z represents a $C_1$-$C_5$-alkylene group or an oxygen or sulfur atom, $R_1$ and $R_2$ represent, e.g., a $C_3$-$C_{12}$-alkyl residue, $C_3$-$C_{12}$-cycloalkyl residue or benzyl residue; and $R_3$, $R_4$, $R_5$ and $R_6$ represent hydrogen or a $C_1$-$C_6$-alkyl residue, comprising the steps of: —heating at least a styrene-polymer component (S) to obtain a molten, polymeric molding compound, —introducing a propellant (T) into the molten molding compound to form a foamable composition (Z), and—foaming the foamable composition to obtain a foamed molding, the molten polymeric molding compound containing at least one carboxylic acid derivative of the general formula (I).

(Continued)

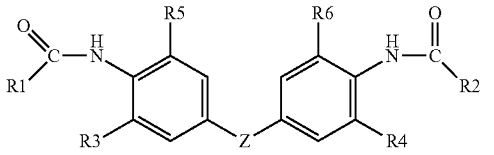

(I)

8 Claims, 2 Drawing Sheets

Figure 1:
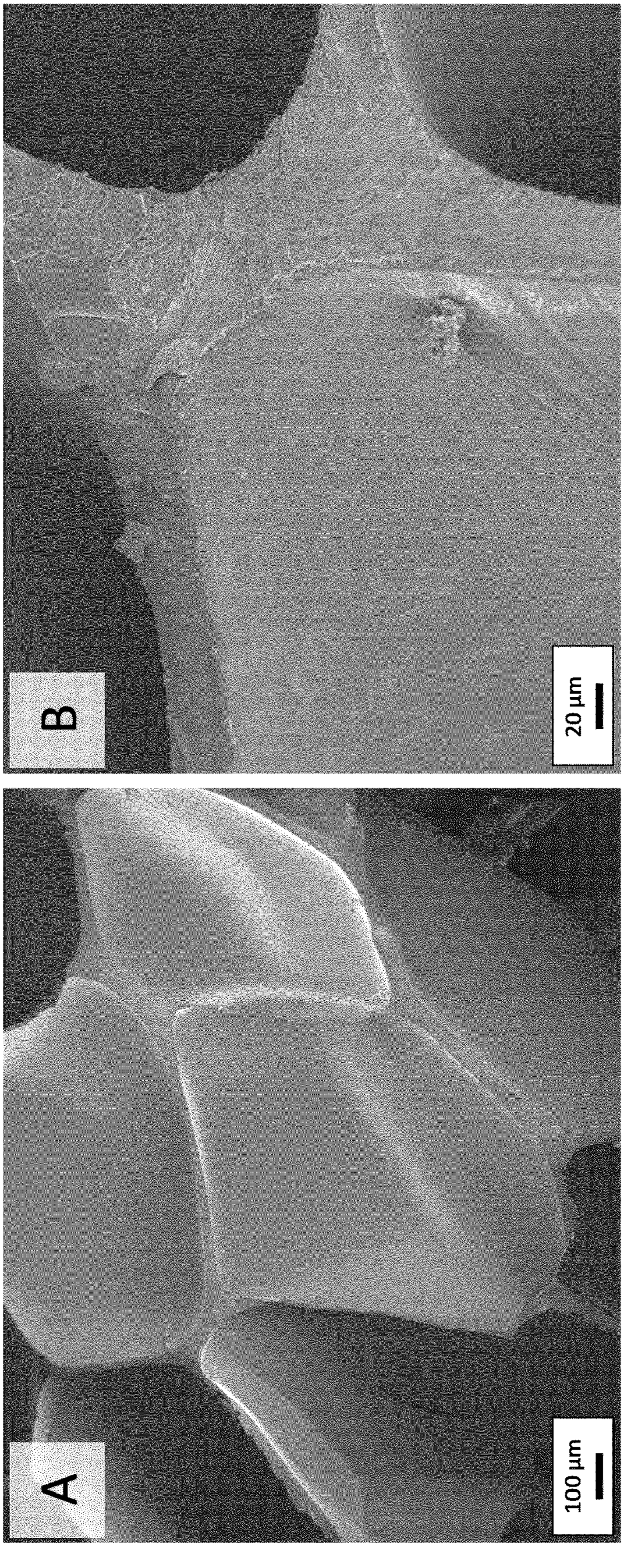

(51) Int. Cl.

| | |
|---|---|
| ***C07C 233/62*** | (2006.01) |
| ***C07C 233/80*** | (2006.01) |
| ***C08J 9/00*** | (2006.01) |
| ***C08K 5/20*** | (2006.01) |

(52) U.S. Cl.
CPC .......... *C07C 233/80* (2013.01); *C08J 9/0028* (2013.01); *C08J 9/122* (2013.01); *C08J 2203/06* (2013.01); *C08J 2205/044* (2013.01); *C08J 2205/052* (2013.01); *C08J 2325/06* (2013.01); *C08J 2325/12* (2013.01)

(58) Field of Classification Search
CPC ...... C08J 9/0028; C08J 9/122; C08J 2203/06; C08J 2205/044; C08J 2205/052; C08J 2325/06; C08J 2325/12; C08J 2201/024; C08J 9/141; C08J 2203/14; C08L 25/06; C08L 25/12
See application file for complete search history.

(56) References Cited

U.S. PATENT DOCUMENTS

| | | | | |
|---|---|---|---|---|
| 8,420,721 | B2 * | 4/2013 | Urushihara .............. | C08K 5/20 524/229 |
| 2005/0261455 | A1 * | 11/2005 | Imai ........................... | C08J 9/16 526/346 |
| 2010/0183863 | A1 | 7/2010 | Linnenbrink et al. | |
| 2015/0166752 | A1 | 6/2015 | Scholz et al. | |
| 2017/0342222 | A1 | 11/2017 | Spijkerman | |

FOREIGN PATENT DOCUMENTS

| | | | |
|---|---|---|---|
| DE | 102011083434 | A1 | 3/2013 |
| EP | 0681522 | A1 | 11/1995 |
| EP | 1031600 | A2 | 8/2000 |
| EP | 1385902 | A2 | 2/2004 |
| EP | 1661939 | A1 | 5/2006 |
| EP | 3083802 | A1 | 10/2016 |
| JP | 2009235250 | A | 10/2009 |
| WO | 2004072168 | A2 | 8/2004 |
| WO | 2015090509 | A1 | 6/2015 |
| WO | 2015197152 | A1 | 12/2015 |

OTHER PUBLICATIONS

M. Morl et al. in Journal of Cellular Plastics 2018, 54, 483-498.
M. Aksit und B. Klose et al. in Journal of Cellular Plastics 2019, 55(3), 249-261.
M. Aksit, C. Zhao et al. in Polymers, 2019, 11, 268ff.
Klose et al: Kinked Bisamides as Efficient Supramolecular Foam Cell Nucleating Agents for Low-Density Polystyrene Foams with Homogeneous Microcellular Morphology, Polymers 2021, 13, 1094.

* cited by examiner

SMALL-CELL POLYSTYRENE FOAMS, AND PROCESS FOR PRODUCING SAME

The present invention relates to a process for producing small-cell foam materials from at least one styrene-containing polymeric material. Other subjects are foams produced by this process, and the use of certain aromatic carboxamides as cell size-reducing additives in foams. These polymer foams are intended preferably to be closed-cell. The mean cell size of the foams as well is to be small and preferably not to vary greatly.

An "open-cell polymer foam", in contrast to closed-cell foam, is understood to be a polymer foam which has at least 20% open cells (based on number of cells), determined according to standard ASTM-D 2856-A (Open-Cell Content in Cellular Plastics).

Various processes for producing foams based on polymers and organic auxiliary components are known from the prior art. Various nucleating agents are added as additives in the literature, especially crystal nucleation and for increasing the transparency, in semicrystalline polymers.

Surprisingly it has emerged that the use of organic angled carboxylic bisamides highly soluble (in the melt) in thermoplastic, styrene-containing polymers enables the production of closed-cell polymer foam of small cell size. The process of the invention is efficient and inexpensive to implement, on both the small and industrial scales. Accordingly, using styrene polymers and these additives, closed-cell polymer foams having a very small mean cell size can be produced, with these foams more particularly having a virtually monomodal cell size distribution.

In the prior art, for example, EP-A 681522 (Dow, 1994) describes a process for producing a polystyrene foam having closed cells, by adding a cell enlarger agent and a blowing agent to a melt and processing the resultant foamable mixture to the foam at relatively low pressure; a polyethylene glycol, for example, is used as an additive.

U.S. Pat. No. 5,210,105 (Dow, 1993) discloses the production of polystyrene foam having a mean cell size of 50-1200 μm.

EP-A 1031600 (BASF, 2000) teaches the production of thick foam sheets of styrene polymers having reduced thermal conductivity and comprising carbon particles. The sheets are used for insulation and have a mean cell count of 4-9, for example, and contain 1% graphite, for example.

EP-B 1385902 (BASF, 2009) discloses a process for producing foams by extruding and foaming a mixture of styrene polymer, 3 to 15 wt % of blowing agent mixture and 0.01 to 10 wt % of graphite particles, the blowing agent used comprising a mixture of carbon dioxide, ethanol, an aliphatic $C_3$-$C_5$ hydrocarbon, and water.

WO 2004/072168 (Ciba) describes the preparation of various tris-carboxamides, which are used as additives in polypropylene products.

EP-A 1661939 (BASF, 2006) describes foams based on styrene polymers having a density in the range from 20 to 200 kg/m$^3$, a mean cell size of 0.08 to 0.25 mm, and a mean cell wall thickness of 350 to 1500 nm. Sheets are produced with reduced thermal conductivity and high compressive strength; the use of specific additives for cell size reduction is not disclosed.

The publication by M. Stumpf et al. in Journal of Cellular Plastics 2011, 47(6), 519-534 teaches the production of various isotactic polypropylene foams using benzene-trisamides as foam nucleating agents.

U.S. Pat. No. 8,420,721 (Adeka, 2013) discloses the synthesis of various aromatic bisamide compounds which are used together with further additives in polyolefins (PE/PP). DE-A 102011083434 (NMB, 2013) describes a process for producing open-cell polymer foams using aromatic trisamide compounds and HMS polypropylene with long-chain branching (Daploy WB 140 HMS, *Borealis*). Nucleating agents used are 1,3,5-tris(2,2-dimethylpropionylamino)-benzene and tris(1,1,3,3-tetramethylbutyl)-1,3,5-benzenetricarboxamide; production takes place via the steps: production of the polymer melt, dissolution of the organic nucleating agent in the melt, addition of blowing agent to the melt, and extrusion of the melt.

WO 2015/090509 and EP-B 3083802 (Clariant) describe the use of aromatic trisamide compounds for producing foamed polymer articles, which may have a density of 10-65 kg/m$^3$, for example. A preferred nucleating additive used is 1,3,5-tris(2,2-dimethylpropionylamino)benzene (Irgaclear® XT 386; BASF, Ludwigshafen, formula (V)) of the formula below. This, however, does not result in uniformly small cell sizes in the polymer foam.

(V)

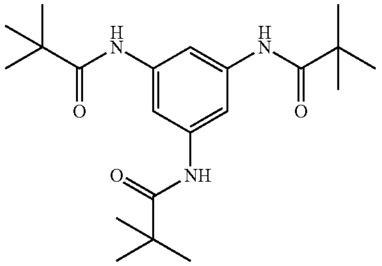

WO 2015/197152 (Clariant) teaches the production of polymer foams, for example polystyrene foam based on polystyrene PS153F (INEOS Styrolution, Frankfurt), using a soluble benzylidene-sorbitol compound of the general formula (VI) as a nucleator during production.

(VI)

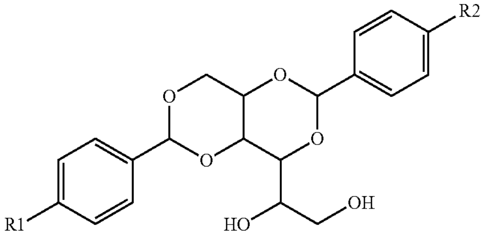

The article by M. Mörl et al. in Journal of Cellular Plastics 2018, 54, 483-498 describes the production of polypropylene foams having medium-size cells, based on Moplen HF400G (Lyondell-Basell) and various aromatic trisamide-based nucleating agents.

The article by M. Aksit and B. Klose et al. in Journal of Cellular Plastics 2019, 55(3), 249-261 teaches the production of polystyrene foam based on polystyrene PS168N (INEOS Styrolution, Frankfurt), using 1,3,5-tris(2,2-dimethylpropionylamino)benzene (Irgaclear XT386, BASF). The density of the PS foam was determined via water displacement (ISO 1183), the structure via electron microscopy (SEM). Uniformly small cell sizes in the polymer foam are not taught.

The publication by M. Aksit, C. Zhao et al. in Polymers, 2019, 11, 268 ff. describes the production of polystyrene foam using benzene-trisamide compounds such as 1,3,5-tris (2,2-dimethylpropionylamino)benzene (Irgaclear XT386, BASF) and mentions a reduction in the thermal conductivity of the foams.

Even when using 0.5 wt % of the nucleating additive, the foam has a cell size of more than 30 micrometers.

Also proposed in the prior art for producing foams from polymeric materials is the addition of graphite or talc; in the production of the foam, the addition of these highly nucleating additives results in relatively small cells, used in amounts above 0.2 wt %, based on the polymeric material. These additives, however, may have adverse consequences for the expansion characteristics of the foam.

In the context of the present invention, a part is played by the density of the foam, but other important factors are the mean cell diameter (D) of the foam (in micrometers) and the structure of the foam (closed-cell) and also the morphology of the cells. The homogeneity of the cells also plays an important part; highly nonuniform cell sizes are a disadvantage in many applications.

An alternative measure that can be stated for the size of the cells, as well as the mean cell diameter, is that of "cells per millimeter" (in each of the three spatial directions per millimeter distance) for the foams produced in the invention. A cell count value of 200 cells per mm describes, for example, a very small-cell foam, while a value of 8 describes, for example, a large-cell foam.

It is an object of the present invention to provide a simple process for producing small-cell foams having (largely) closed cells, starting from styrene-containing polymers and from inexpensively preparable additives. The size and structure of the foam cells can be analyzed by the methods described later on.

This object is achieved by means of a process for producing a foam from at least one styrene polymer component (S) and at least one additive of the general formula (I), and the process comprises the steps of:

a. heating at least one styrene polymer component (S) to give a melted polymeric molding compound,
b. introducing a blowing agent (T) into the melted polymeric molding compound, to form a foamable composition (Z), and
c. foaming the foamable composition (Z) to give a foamed molding, wherein at least one carboxamide of the general formula (I) is used in the melted polymeric molding compound, (I)

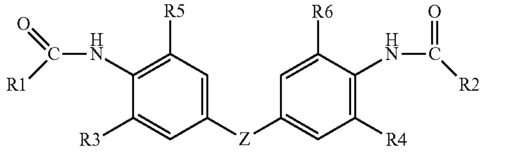

wherein:

Z is a $C_1$-$C_5$, more particularly $C_1$-$C_3$ alkylene group, often —$CH_2$—, or an oxygen atom or sulfur atom, often an oxygen atom;

R1 and R2 independently of one another are a branched $C_3$-$C_{12}$ alkyl radical or unbranched $C_1$-$C_{12}$ alkyl radical, a $C_3$-$C_{12}$ cycloalkyl radical, or a benzyl radical;

R3, R4, R5 and R6 each independently of one another are hydrogen, an unbranched $C_1$-$C_6$ alkyl radical or a branched $C_3$-$C_6$ alkyl radical.

The process for producing a foam from styrene polymer component (S) and additive of the formula (I) may involve various typical processes for producing polymer foams.

It may be a simple "batch foam process" (on the small scale), in which a blowing agent (T) is introduced via a pump into an autoclave containing the polymer composition.

Alternatively it may be an (e.g., industrial) foam extrusion process in which, for example, a polystyrene (and/or a styrene copolymer) and the additive or additives are introduced into an extruder (e.g., twin-screw extruder) and heated (e.g., 260° C.), then the blowing agent is injected, in order then to supply the composition, optionally via a further extruder (with lower temperature), to the foam-forming unit.

The "angled" aromatic carboxamide compounds (derivatives) used as additive are bisamides and preferably contain a methylene group as group Z. They are preferably readily soluble in the polymers used, especially at the processing temperature.

In one embodiment of the invention, in the general formula (I), R1 and R2 independently of one another are a $C_3$-$C_{12}$ cycloalkyl radical, more particularly a cyclohexyl radical or cyclopentyl radical, a butyl radical or a benzyl radical.

In one embodiment of the invention, in the general formula (I), Z is a methylene group and R3, R4, R5 and R6 each independently of one another are a $C_1$-$C_6$ alkyl radical, more particularly a $C_1$-$C_2$ alkyl radical.

In one embodiment of the invention, in formula (I), Z is a —$CH_2$ group or an oxygen atom; R1 and R2 independently of one another are a branched or unbranched $C_4$-$C_6$ alkyl radical, a $C_5$-$C_6$ cycloalkyl radical, or a benzyl radical; and R3, R4, R5 and R6 each independently of one another are hydrogen or an unbranched $C_1$-$C_3$ alkyl radical, more particularly a methyl or ethyl radical.

In one embodiment of the invention, in the process, the carboxylic bisamide derivative of the general formula (I) is used in an amount of 0.01 to 2.0 wt %, more particularly 0.05 to 1.0 wt %, often 0.1 to 0.5 wt %, based on the total weight of the polymeric molding compound.

In one embodiment of the invention, in the process, a blowing agent (T) from the group of pentane, cyclopentane, carbon dioxide and ethanol or a mixture (of two or more components) is introduced into the melted polymeric molding compound.

In one embodiment of the invention the styrene polymer component (S) used is a polystyrene (PS) or a copolymer containing styrene and acrylonitrile, more particularly styrene-acrylonitrile (SAN). A mixture of PS and other styrene polymer components can also be used.

The invention also relates to a foam obtainable (or obtained) by a process according to at least one of the abovementioned embodiments.

This foam preferably has a density in the region of at least 30 kg/$m^3$, more particularly 45-85 kg/$m^3$, often 60-85 kg/$m^3$ (especially in the case of polystyrene) This foam has an at least 50% closed-cell structure, preferably an at least 80%, more particularly at least 90%, often at least 95% closed-cell structure.

This foam has a mean cell diameter (D) of 0.1-25.0, frequently of 1.0-16.0, preferably 2.0-15.0, often 3.0 to less than 15.0 micrometers.

The foam preferably also has a virtually uniform mean cell size (small standard deviation in the diameter) and a uniform cell morphology, e.g. of honeycomb form, as may be analyzed by SEM micrographs.

The foam is preferably a polystyrene-based foam or a styrene-acrylonitrile copolymer-based foam.

Another subject of the invention is a polymer composition for producing a foam, comprising at least one styrene polymer component (S) and at least one carboxamide of the general formula (I) and also optionally further additives,

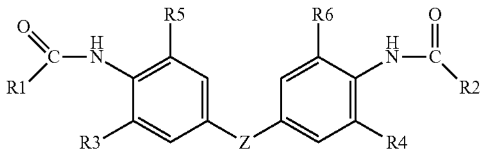
(I)

wherein the substituents Z, R1 and R2, and R3, R4, R5 and R6 have the definitions stated above in each case.

The invention also relates to the use of a carboxamide of the general formula (I), wherein the substituents Z, R1 and R2, and R3, R4, R5 and R6 have the definitions stated above in each case,

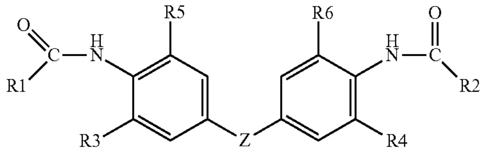
(I)

as an additive reducing the mean cell diameter (D) of a foam in the production of foams from at least one polymeric material, more particularly at least one styrene polymer component (S).

Particularly good results in respect of small-cell foams, high fraction of closed cells and also uniform size of the cells are achieved when using polystyrene and SAN copolymers.

Another subject of the invention is a process for preparing a carboxamide of the general formula (I), wherein the substituents Z, R1 and R2, and R3, R4, R5 and R6 have the definitions stated above in each case, by reacting at least one activated carboxylic acid derivative with an (aromatic) bisamine derivative.

Further subjects of the invention are also the carboxamides of the general formula (I) themselves, especially when Z is a $-CH_2$ group, R1 and R2 independently are benzyl, cyclohexyl, n-butyl, tert-butyl; and R3, R4, R5 and R6 each independently are methyl or ethyl. The compounds from the examples are of particular interest.

By means of the carboxamides of the general formula (I) employable in the invention it is possible to adjust the cell size of a foam produced in the presence of said carboxamides to an optimal value.

Additionally, foams are obtained which have largely (at least 80%, frequently at least 90%, often at least 95%) closed cells, which may be verified, for example, by microscope analysis.

Through the use of the bisamides of the formula (I) in the invention it becomes possible to achieve a marked reduction in the size of the cells during foaming and a desiredly uniform morphology, hence enabling the production of improved moldings from the foam.

In the process of the invention, a foam is produced in a few steps from at least one styrene-containing polymeric material. The styrene polymer component (S) used is generally a homopolymer or copolymer. Suitable polymers include homopolymers of styrene monomers (e.g., styrene, alpha-methylstyrene, ring-substituted styrenes) but also copolymers of styrene monomers and ethylenically unsaturated monomers copolymerizable with styrene.

The latter, for example, are acrylonitrile, maleic anhydride, methyl acrylate, ethyl acrylate, methyl methacrylate, vinyl acetate, butadiene, divinylbenzene and butanediol diacrylate. These comonomers are sometimes used only in small amounts, in order to ensure foaming.

In one preferred embodiment the styrene polymer component (S) is composed of at least 50 wt %, preferably at least 70 wt %, of styrene monomers and of at most 50 wt %, preferably at most 30 wt %, of a further monomer, e.g., acrylonitrile.

In one preferred embodiment the styrene polymer component (S) is a polystyrene. It preferably contains more than 95 wt % of polystyrene (PS). Styrene-acrylonitrile (SAN) is also a preferred component (S), optionally mixed with polystyrene.

In a further embodiment, in addition to the styrene polymer component (S), up to 50 wt %, based on the overall polymer composition, of a further polymer is also used, for example a PMMA or PVC.

The styrene homopolymers and copolymers which can be used in the invention may be produced by known processes, for example by radical or ionic polymerization, in bulk, solution or emulsion. Radical polymerization is preferred. They generally have weight-average molecular weights (Mw) of 100 000 to 400 000 g/mol, preferably 120 000 to 350 000 g/mol.

In step (a) of the process of the invention, the polymeric material (S) is heated or warmed to give a melted polymeric molding compound. This requires that the styrene polymer component (S) is heated to a temperature above the melting temperature or glass transition temperature. Suitable temperatures are generally 100 to 280° C., preferably 180 to 260° C. If polystyrene is used, the component (S) must generally be heated to a temperature of 180° C. or more in order to obtain a melt.

A foamable polymer melt can be generated in extruders known to the skilled person, for example by way of a tandem construction composed of melting extruder and secondary extruder. Step (a) of the process of the invention may be carried out continuously and batchwise, preferably continuously, with the styrene polymer component (S) being melted in the melting extruder.

By addition of a blowing agent (T) in the primary and/or secondary extruder, for example, a foamable composition is then formed, which is able to generate a continuous foam at the die.

Step (b) of the process of the invention comprises introducing at least one blowing agent (T) into the styrene polymer component (S), melted in step (a), to form a foamable composition. Suitable blowing agents (T) include, in particular, inorganic and organic blowing agents. Suitable inorganic blowing agents include carbon dioxide, nitrogen, argon, water, air and helium. One frequently used blowing agent, for example, is a mixture of carbon dioxide and water.

Organic blowing agents are, for example, aliphatic hydrocarbons having 1-9 carbon atoms and fully or partly halogenated aliphatic hydrocarbons having 1-4 carbon atoms. Aliphatic hydrocarbons are, for example, methane, ethane, propane, n-butane, isobutene, n-pentane, isopentane, and neopentane. Fully and partly halogenated aliphatic hydrocarbons are, in particular, fluorocarbon compounds, chlorocarbon compounds and chlorofluorocarbon compounds. Examples of fluorocarbon compounds are methyl fluoride, perfluoromethane, ethyl fluoride, difluoromethane, 1,1-difluoroethane, 1,1,1-trifluoroethane, 1,1,1,2-tetrafluoroethane, pentafluoroethane, difluoromethane, perfluoroethane, 2,2-difluoropropane, 1,1,1-trifluoropropane, perfluoropropane, difluoropropane, difluoropropane, perfluorobutane, perfluorocyclopentane.

Partly halogenated chlorocarbon compounds and chlorofluorocarbon compounds suitable for use in the process of the invention include methyl chloride, methylene chloride, ethyl chloride, 1,1,1-trichloroethane, chlorodifluoromethane, 1,1-dichloro-1-fluoroethane, 1-chloro-1,1-difluoroethane, 1,1-dichloro-2,2,2-trifluoroethane and 1-chloro-1,2,2,2-tetrafluoroethane. Fully halogenated hydrochlorofluorocarbon compounds include trichloromonofluoromethane, dichlorodifluoromethane, trichlorotrifluoroethane, 1,1,1-trifluoroethane, pentafluoroethane, dichlorotetrafluoroethane, chloroheptafluoropropane and dichlorohexafluoropropane.

Further suitable chemical blowing agents (T) are azodicarboxamide, azodiisobutyronitrile, benzenesulfono-hydrazide, 4,4-oxybenzenesulfonyl semicarbazide, p-toluenesulfonyl semicarbazide, barium azo-dicarboxylate, N,N'-dimethyl-N,N'-dinitrosoterephthalamide and trihydrazinotriazine.

A further blowing agent mixture comprises 20 to 95 wt % of carbon dioxide, 5 to 80 wt % of water and 0 to 75 wt % of an alcohol, for example methanol or ethanol, a ketone or an ether.

For environmental reasons it is often desirable to use inorganic blowing agents. Two popular inorganic blowing agents are carbon dioxide and water.

The amount of the blowing agent (T) introduced into the melted styrene polymer component (S) to give a foamable composition (Z) is 0.1-20, preferably 0.5-15, often 1.0-10 wt %, based on the mass of the styrene polymer component (S).

The blowing agent may be introduced into the styrene polymer component (S) by various known methods, for example by means of an extruder, a mixer or a blender. The blowing agent is mixed at elevated pressure with the melted polymer material, for example. The pressure is high enough to substantially prevent expansion of the melted polymer material and to enable uniform distribution of the blowing agent (T) in the melted styrene polymer component (S). Examples of suitable pressures are 100 to 200 bar (absolute), preferably 150 to 170 bar (absolute).

The temperature in step (b) of the process of the invention is selected such that the polymeric material is in the melted state. Step (b) of the process of the invention is therefore carried out generally at 100-180° C. Step (b) may be carried out continuously or batchwise, preferably continuously.

In one preferred embodiment the melted styrene polymer component (S) is admixed with at least one carboxamide derivative as described above.

The bisamides and further additives may be added, for example, in step (a) and/or (b) of the process. The addition may be made in the form of a powder-powder mixture or, for example, via a masterbatch, both in step (a) and in step (b), preferably in step (a).

Step (c) of the process of the invention comprises the foaming of the foamable composition (Z) to give a foamed molding (the foam).

In one preferred embodiment this foaming is obtained by extrusion of the melted styrene polymer component (S) containing blowing agent (T) through a suitable apparatus, a die for example, into a region of lower pressure (than used in step (b)). Step (c) is likewise carried out at a temperature at which the composition for foaming is in the melted state, generally 80-125° C., preferably 110-125° C.

As a result of the melted polymeric material containing a blowing agent being transferred in step (c) into a region in which a lower pressure is prevailing, the blowing agent is converted into the gaseous state. The large increase in volume causes expansion and foaming of the polymeric material.

The process of the invention is characterized in that a carboxylic bisamide of the general formula (I) stated above is used in the melted styrene polymer component (S).

In one particularly preferred embodiment the carboxylic bisamide is selected from the group of the compounds stated in the examples, and mixtures thereof.

The carboxylic bisamides of the formula (I) which can be used in the invention may be obtained by processes known to the skilled person, for example by, optionally catalyzed, reaction of the corresponding carboxylic acids (or activated derivatives) with the corresponding amines.

The at least one carboxylic bisamide (I) is used in the process of the invention in general in an amount of 0.01 to 2 wt %, preferably 0.1 to 2 wt %, more preferably 0.2 to 1.0 wt %, for example 0.1 to 0.5 wt %, based in each case on the total weight of the polymeric molding compound.

The at least one carboxylic bisamide of the formula (I) may be added to the polymeric molding compound in steps (a) or (b) of the process of the invention. Suitable procedures are, for example, the metering of the carboxylic bisamide into the melting zone of the extruder to the polymeric material.

The foam obtainable by the process of the invention is notable for a reduced size of the cells.

In general in the foam produced in the invention there are a very large number of cells (>150) per mm (in each spatial direction) of the foam.

The low mean cell size of the foam may be measured by methods known to the skilled person, for example scanning electron microscopy. The aforementioned low cell size and the homogeneous size distribution are attributable to the use of the specific carboxamides of the formula (I) in the process of the invention.

The carboxamides used mean that the polymeric material can be foamed in a particularly effective way, with the consequence, for example, that foam sheets having relatively high thicknesses (e.g., greater than 60 mm) are also obtainable directly. These sheets have good insulating properties.

In the process of the invention it is possible optionally for further additives to be introduced into the foam, for example inorganic fillers, pigments, antioxidants, acid scavengers, UV absorbers, flame retardants, processing aids and extrusion aids. These further additives are used generally in an amount of 0.1 to 2 wt %, based in each case on the overall polymeric molding compound. These additives may already be present in the polymeric material before step (a), or are added to the polymeric material in step (a) and/or (b).

As (further) nucleating agents it is possible to use finely divided inorganic solids such as talc, metal oxides, silicates or polyethylene waxes in amounts of in general 0.1 to 1.0 wt %, based on the styrene polymer component (S). The mean particle diameter of this nucleating agent is generally in the range from 0.01 to 100 μm, preferably 20 to 60 μm. The nucleating agent may be added to the polymer melt by known methods.

The foam produced by the present process may also be used for insulating surfaces, by applying to said surface an insulating layer of the foam produced in the invention. This may be carried out in all known insulating applications, for example on rooves, buildings and household appliances, such as refrigerators.

The foam produced in the invention may be shaped into a multiplicity of shaped foamed parts, for example for packaging, or into solid workpieces of suitable size.

The present invention also relates to the use of at least one carboxylic bisamide of the general formula (I) with the meanings defined above in the foaming of at least one styrene polymer component (S).

The present invention also relates to a foam obtainable (or obtained) by the process of the invention. In the analyses of the foams for their morphology, size and physical properties, numerous results have been obtained. The figures which follow are elucidated by way of example.

FIG. 1 shows two scanning electron micrographs (A at 50 times magnification and B at 250 times magnification) of cells of a (pure) polystyrene foam ("neat PS") produced without addition of a bisamide of the formula (I). The foam is based on commercial polystyrene PS 168N (INEOS STYROLUTION, Frankfurt). It is clearly apparent that the cells of the foam have a large mean cell size. The cell size distribution of the PS foam is also nonuniform.

Figure 2:
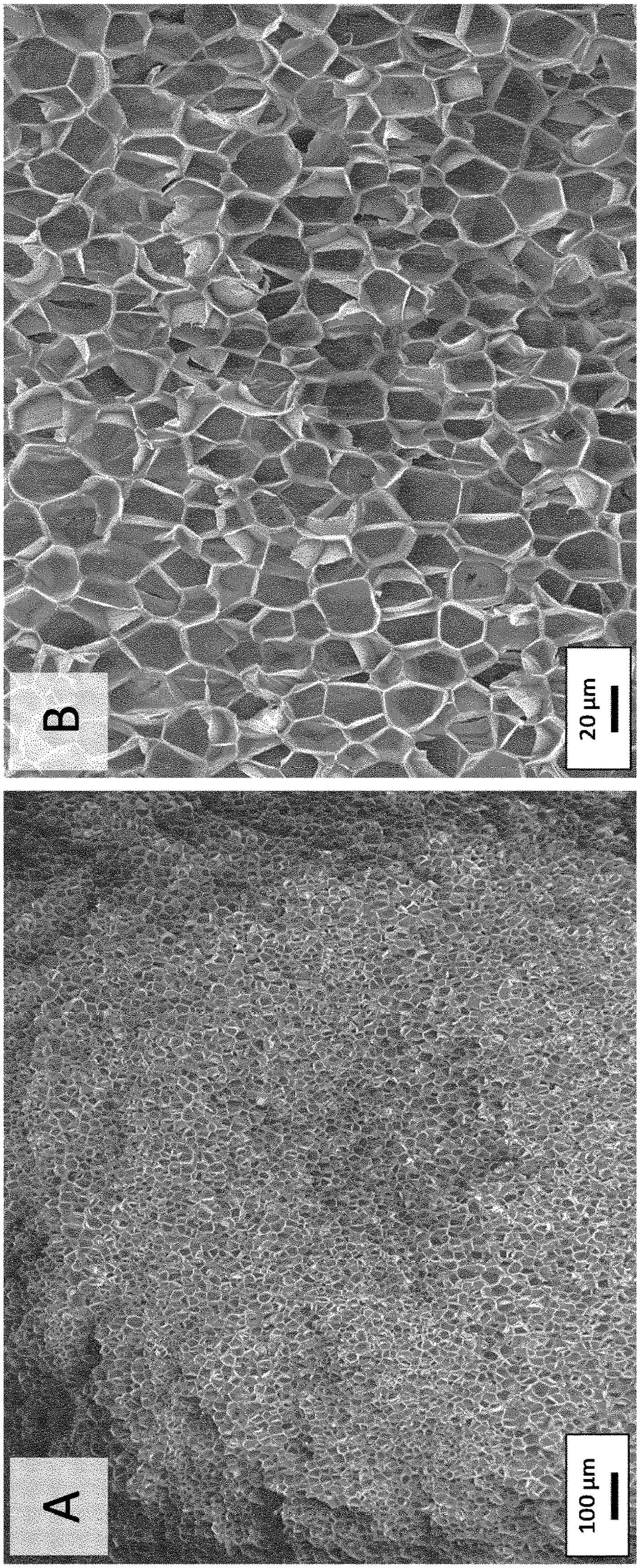

FIG. 2 shows two scanning electron micrographs (A at 50 times magnification and B at 250 times magnification) of cells of a polystyrene foam produced using the bisamide of the formula (I). The foam is based on polystyrene PS168N (INEOS STYROLUTION). In this case the additive used as component (3b) was the compound N,N'-[methylenebis(2,6-diethyl-4,1-phenylene)]biscyclo-hexanecarboxamide] in an amount of 0.1 percent by weight.

It is clearly apparent that the morphology of the cells of the foam is closed-cell and small-cell. A small mean cell size (14.4+/−4.7 micrometers) and a narrow cell size distribution are evident.

The polystyrene foam here has a cell density of $4.3\times10^8$ $cm^{-3}$ and also a foam density of 76.5 kg/$m^3$. There is also no pronounced bimodal cell size distribution in the foam, as often occurs in the case of other additives, such as trisamide derivatives, for example.

The invention is further elucidated in more detail by the following examples and claims.

EXAMPLES

The "angled" carboxylic bisamide derivatives used may be synthesized according to the processes described below; all chemicals for the preparation are available commercially and can be used without further purification.

The medium-viscosity silicone oil M100 (Carl Roth GmbH+Co. KG) was used as the oil bath for the foaming of the samples in the batch foam process. The blowing agent $CO_2$ with 99.995% purity was purchased from Rießner Gase GmbH.

Characterization took place using the following analytical methods and techniques:

Differential scanning calorimetry (DSC): DSC analyses were carried out using a Mettler Toledo DSC 2. Around 6-12 mg of a compound were weighed out in a 30 μL high-pressure crucible to this end. The angled bisamide derivatives 1a-d, 2a, 2d, 3a and 3d were measured in a temperature range of 25-300° C. and the angled bisamide derivatives 2b-c and 3b-c in a temperature range of 25-350° C., in each case with a rate of 10 K/min. Each heating and cooling step was repeated three times. The recorded melting points were taken from the second heating step.

Mass spectrometry (MS): MS analyses were carried out using electron spray ionization on a customary instrument (FINNIGAN MAT 8500 spectrometer from Thermo-Fisher Scientific).

Scanning electron microscopy (SEM): Scanning electron micrographs were recorded on a customary microscope (Zeiss LEO 1530) with an acceleration voltage of 3 kV and using an internal lens detector or SE2 detector.

For this analysis, the foam samples were first cryofractured with liquid nitrogen and the fracture edges were sputter-coated with 2 nm of platinum under an argon atmosphere using a coater (Cressington Sputter Coater 208HR). Prior to sputtering, the samples were additionally lined on the sides with self-adhesive copper foil, in order to ensure better conductivity.

Thermal conductivity: The thermal conductivity of the foam samples was measured with a customary heat flow meter (LaserComp FOX 50 from TA Instruments). The foam samples were cut into cylinders 60 mm in diameter with a thickness (L) of between 3 mm and 8 mm, depending on the extruded thickness of the foam. The samples were positioned between two temperature-conditioned plates.

The temperature of the upper plate was adjusted to 30° C. and that of the lower plate to 20° C., producing a temperature difference (ΔT) of 10° C. along the sample thickness. The resulting heat flow (Q/A) through the foam sample was measured by means of two thin-film heat flow transducers. The thermal conductivities (t) were calculated according to formula (1):

$$\lambda_t = \frac{Q \cdot L}{A \cdot \Delta T} \tag{1}$$

At least five samples of each foam were measured at different positions and average values for the thermal conductivity were determined.

Foam density: The foam density was determined by the water displacement method according to standard ISO 1183, using an analytical balance (Mettler Toledo XP 205) with density kit. For this analysis, small blocks were cut from the samples and weighed in air ($m_{air}$). After that, the buoyancy of the samples underwater was determined. ($m_{water}$; $\rho_{water}$: density of the water at measurement temperature). The resulting density ($\rho_{foam}$) was calculated using the following equation:

$$\rho_{foam} = \frac{m_{air}}{m_{air} - m_{water}} \cdot \rho_{water}$$

Each measurement was carried out with three different blocks of the sample in question, and the average value was recorded.

Morphology: The morphology of the foam samples was analyzed by means of SEM micrograph. A region ($A_{cell}$) of at least 70 cells of each sample was considered. On the assumption of a circular shape to the cells, the following equation was employed for determining the size (Φ) of all the individual cells:

$$\Phi = 2 \cdot \sqrt{\frac{A_{cell}}{\pi}}$$

The arithmetic mean ((D) of all the calculated cells, with standard deviation, is listed for each foam.

Example 1 Preparation of the Carboxylic Bisamide Derivatives of the Formula (I)

Starting from the corresponding aromatic bisamine compounds and acid derivatives, the aromatic bisamide derivatives below were prepared, and are readily soluble in the polymer (PS, SAN) at processing temperature.

Compounds 1a-d, 2a-d, 3a-d were purified and characterized. The syntheses of these bisamide additives of the formula (I) are described below.

1a Synthesis of N,N'-[methylenebis(4,1-phenylene)] bis-[benzamide]

5 g (25.2 mmol) of 4,4'-diaminodiphenylmethane, 4.5 mL of pyridine and 100 mL of NMP were mixed in a Schlenk flask and cooled to around 0-5° C. Under an argon atmosphere, 7.79 g (55.4 mmol) of benzoyl chloride were added dropwise and the mixture was subsequently warmed to room temperature. After an hour, the reaction mixture was precipitated from ice-water and the solid obtained was isolated by filtration and dried. For further purification, the solid was heated at reflux in 500 mL of MeOH, filtered and dried under a high vacuum. 9.65 g (95%) of the product 1a were obtained in the form of a white powder. Characterization: MS: (70 eV), m/z (%): 406 [$M^+$]; DSC: $T_m$=249° C.

1b Synthesis of N,N'-[methylenebis(4,1-phenylene)] bis-[cyclohexanecarboxamide]

3 g (15.0 mmol) of 4,4'-diaminodiphenylmethane, 20 mL of pyridine, 100 mL of NMP and LiCl were mixed in a Schlenk flask and cooled to around 0-5° C. Under an argon atmosphere, 4.9 g (33 mmol) of cyclohexanecarbonyl chloride were added dropwise. The reaction mixture was subsequently heated at 80° C. for 12 h and then precipitated from ice-water. The solid obtained was isolated by filtration and dried. For further purification, the solid was recrystallized in 500 mL of MeOH, filtered and dried under a high vacuum. 5.5 g (88%) of the product 1b were obtained in the form of a white powder. Characterization: (88%); MS: (70 eV), m/z (%): 418 [$M^+$]; DSC: $T_m$=221° C.

1c Synthesis of N,N'-[methylenebis(4,1-phenylene)] bis-[2,2-dimethylpropanamide]

3 g (15 mmol) of 4,4'-diaminodiphenylmethane, 20 mL of pyridine, 100 mL of NMP and LiCl were mixed in a Schlenk flask and cooled to around 0-5° C. Under an argon atmosphere, 4 g (33 mmol) of pivaloyl chloride were added dropwise. The reaction was stirred at 80° C. for 12 h, followed by precipitation from ice-water. The resulting solid was isolated by filtration and dried. For further purification, the solid was recrystallized in 500 mL of ethyl acetate, isolated by filtration and dried under a high vacuum. 4.1 g (75%) of the product 1c were obtained in the form of a white powder. Characterization: MS: (70 eV), m/z (%): 366 [$M^+$]; DSC: $T_m$=239° C.

1d Synthesis of N,N'-[methylenebis(4,1-phenylene)] bis-[pentanamide]

5 g (25.21 mmol) of 4,4'-diaminodiphenylmethane, 4.5 mL of pyridine and 100 mL of NMP were mixed in a Schlenk flask and cooled to around 0-5° C. Under an argon atmosphere, 6.02 g (55.47 mmol) of valeroyl chloride were added dropwise and the mixture was warmed to room temperature. After a reaction time of one hour, the mixture was precipitated from ice-water. The resulting solid was then isolated by filtration and dried. For further purification, the solid was recrystallized in 300 mL of MeOH, filtered and dried under a high vacuum. 8.8 g (95%) of the product 1d were obtained in the form of a white powder. Characterization: MS: (70 eV), m/z (%): 366 [$M^+$]; DSC: $T_m$=192° C.

2a Synthesis of N,N'-[methylenebis(2,6-dimethyl-4, 1-phenylene)]bis[benzamide]

5 g (19.65 mmol) of 4,4'-methylenebis(2,6-dimethyl-aniline), 3.5 mL of pyridine and 100 mL of NMP were mixed in a Schlenk flask and cooled to around 0-5° C. Under an argon atmosphere, 6.07 g (43.23 mmol) of benzoyl chloride were added dropwise and the mixture was warmed to room temperature. After an hour, the reaction mixture was precipitated from ice-water. The resulting solid was then isolated by filtration and dried. For further purification, the solid was heated under reflux in 500 mL of MeOH, filtered and dried under a high vacuum. 7.5 g (82%) of the product 2a were obtained in the form of a white powder. Characterization: MS: (70 eV), m/z (%): 462 [$M^+$]; DSC: $T_m$=225° C.

2b Synthesis of N,N'-[methylenebis(2,6-dimethyl-4, 1-phenylene)]bis[cyclohexanecarboxamide]

3.56 g (14.00 mmol) of 4,4'-methylenebis(2,6-dimethyl-aniline), 4.28 mL of $Et_3N$ and 100 mL of THF were mixed in a Schlenk flask and cooled to around 0-5° C. Under an argon atmosphere, 4.51 g (30.76 mmol) of cyclohexanecarbonyl chloride were added dropwise. After 48 h at 60° C., the reaction mixture was precipitated from ice-water. The resulting solid was then isolated by filtration, washed with water and subsequently dried. For further purification the solid was recrystallized in 250 mL of DMF, filtered and dried under a high vacuum. 5.6 g (84%) of the product 2b (formula (II)) were obtained in the form of a white powder. Characterization: MS: (70 eV), m/z (%): 474 [$M^+$]; DSC: $T_m$=307° C.

(II)

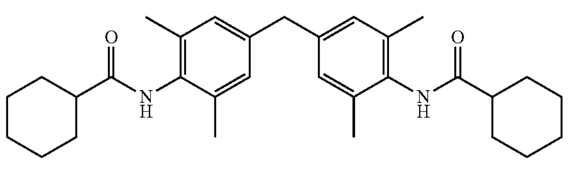

2c Synthesis of N,N'-[methylenebis(2,6-dimethyl-4, 1-phenylene)]bis[2,2-dimethylpropanamide]

4 g (15.72 mmol) of 4,4'-methylenebis(2,6-dimethyl-aniline), 2.8 mL of pyridine and 100 mL of THF were mixed in a Schlenk flask and cooled to around 0-5° C. Under an argon atmosphere, 4.17 g (34.59 mmol) of pivaloyl chloride were added dropwise and the mixture was warmed to room temperature. After an hour the reaction mixture was precipitated from ice-water. The solid was then isolated by filtration and dried. For further purification the solid was first recrystallized in 100 mL of MeOH, followed by filtration over silica gel with DMF as eluent. The solvent was removed by concentration and the solid was precipitated from water and dried at 80° C. 4.9 g (74%) of the product 2c were obtained in the form of a white powder. Characterization: MS: (70 eV), m/z (%): 422 [$M^+$]; DSC: $T_m$=310° C.

2d Synthesis of N,N'-[methylenebis(2,6-dimethyl-4,1-phenylene)]bis[pentanamide]

3 g (11.79 mmol) of 4,4'-methylenebis(2,6-dimethyl-aniline), 2.4 mL of pyridine and 200 mL of THF were mixed in a Schlenk flask and cooled to around 0-5° C. Under an argon atmosphere, 2.81 g (25.94 mmol) of valeroyl chloride were added dropwise and the mixture was warmed to room temperature. After an hour, the reaction mixture was precipitated from ice-water. The solid was then isolated by filtration and dried. For purification, the solid was recrystallized in 300 mL of MeOH, filtered and dried under a high vacuum. 3.6 g (72%) of the product 2d were obtained in the form of a white powder. Characterization: MS: (70 eV), m/z (%): 422 [$M^+$]; DSC: $T_{m1}$=190° C., $T_{m2}$=258° C.

3a Synthesis of N,N'-[methylenebis(2,6-diethyl-4,1-phenylene)]bis[benzamide]

5 g (16.10 mmol) of 4,4'-methylenebis(2,6-diethyl-aniline), 2.8 mL of pyridine and 100 mL of NMP were mixed in a Schlenk flask and cooled to around 0-5° C.

Under an argon atmosphere, 4.98 g (35.42 mmol) of benzoyl chloride were added dropwise and the mixture was warmed to room temperature. After an hour, the reaction mixture was precipitated from ice-water. The resulting solid was then isolated by filtration and dried. For further purification, the solid was heated under reflux in 500 mL of MeOH, filtered and dried under a high vacuum. 7.0 g (83%) of the product 3a were obtained in the form of a white powder. Characterization: MS: (70 eV), m/z (%): 518 [$M^+$]; DSC: $T_m$=258° C.

3b Synthesis of N,N'-[methylenebis(2,6-diethyl-4,1-phenylene)]bis[cyclohexanecarboxamide]

9 g (28.00 mmol) of 4,4'-methylenebis(2,6-diethyl-aniline), 5.1 mL of pyridine and 120 mL of NMP were mixed in a Schlenk flask and cooled to around 0-5° C. Under an argon atmosphere and with ice cooling, 9.34 g (63.00 mmol) of cyclohexanecarbonyl chloride were added dropwise and the mixture was warmed to room temperature. After a reaction time of two hours, 100 mL of water was added to the mixture, which was stirred for a further hour and then the solid was filtered. For further purification the solid was heated under reflux in 200 mL of acetone, filtered and dried under a high vacuum. 14.2 g (92%) of the product 3b (formula (III)) were obtained in the form of a white powder. Characterization: MS: (70 eV), m/z (%): 530 [$M^+$]; DSC: $T_m$=297° C.

(III)

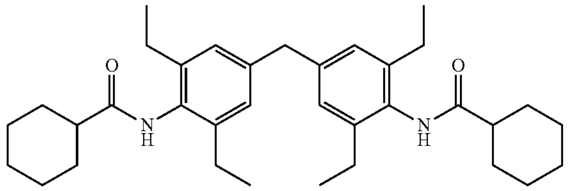

3c Synthesis of N,N'-[methylenebis(2,6-diethyl-4,1-phenylene)]bis[2,2-dimethylpropanamide]

4.34 g (14.00 mmol) of 4,4'-methylenebis(2,6-diethyl-aniline), 4.3 mL of $Et_3N$ and 50 mL of THF were mixed in a Schlenk flask and cooled to around 0-5° C. Under an argon atmosphere, 3.71 g (30.80 mmol) of pivaloyl chloride were added dropwise and the reaction mixture was heated to 60° C. After 48 h the mixture was precipitated from ice-water. The resulting solid was then isolated by filtration and recrystallized in 500 mL of MeOH. For further purification, the solid was recrystallized in 250 mL of DMF, filtered and dried under a high vacuum. 4.8 g (71%) of the product 3c were obtained in the form of a white powder. Characterization: MS: (70 eV), m/z (%): 478 [$M^+$]; DSC: $T_m$=328° C.

3d Synthesis of N,N'-[methylenebis(2,6-diethyl-4,1-phenylene)]bis[pentanamide]

4.34 g (14.00 mmol) of 4,4'-methylenebis(2,6-diethyl-aniline), 4.3 mL of $Et_3N$ and 50 mL of THF were mixed together in a Schlenk flask and cooled to around 0-5° C. Under an argon atmosphere, 3.71 g (30.8 mmol) of valeroyl chloride were added dropwise, followed by heating to 50° C. After 3 h, the reaction mixture was precipitated from ice-water. The resulting solid was then isolated by filtration and washed with $H_2O$. For further purification, the solid was recrystallized in 200 mL of MeOH, filtered and dried under a high vacuum. 3.7 g (56%) of the product 3d (formula (IV)) were obtained in the form of a white powder. Characterization: MS: (70 eV), m/z (%): 478 [$M^+$]; DSC: $T_{m1}$=120° C., $T_{m2}$=220° C.

(IV)

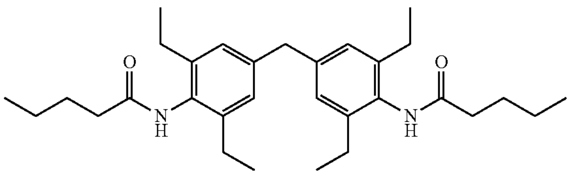

All carboxylic bisamides depicted in table 1 below are subject to the formula (I). They can be prepared readily even in substantial quantities. The stated compounds are soluble in polystyrene and SAN at processing temperature.

TABLE 1

Angled bisamides of the general formula (I) used

| | Bisamide additive | Substituents $R_3$, $R_4$, $R_5$, $R_6$ | Substituents $R_1$, $R_2$ |
|---|---|---|---|
| 1 | a | H | Benzyl |
| | b | | Cyclohexyl |
| | c | | tert-Butyl |
| | d | | n-Butyl |
| 2 | a | Methyl | Benzyl |
| | b | | Cyclohexyl |
| | c | | tert-Butyl |
| | d | | n-Butyl |
| 3 | a | Ethyl | Benzyl |
| | B | | Cyclohexyl |
| | C | | tert-Butyl |
| | D | | n-Butyl |

Example 2 Comparative Carboxamide Derivatives

For the comparative experiments, firstly the trisamide additive Irgaclear® XT 386 (BASF SE) and secondly the bisamide additive NJ Star NU100 (N,N'-dicyclohexyl-2,6-naphthalenedicarboxamide) of New Japan Chemical were used.

The symmetrical aromatic trisamide Irgaclear® XT 386 used as a transparency booster for polypropylene (1,3,5-tris (2,2-dimethylpropionylamino)benzene; BASF, formula (V)) may be prepared analogously from 1,3,5-trisaminobenzene and acyl chloride.

(V)

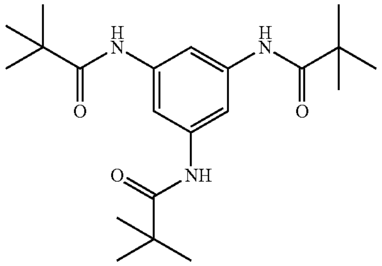

A (nonangled) aromatic bisamide derivative may be prepared from naphthalene-2,6-dicarboxylic acid and cyclohexylamine. It is also sold by New Japan Chemical as product NJ STAR NU100 (formula (VII)).

(VII)

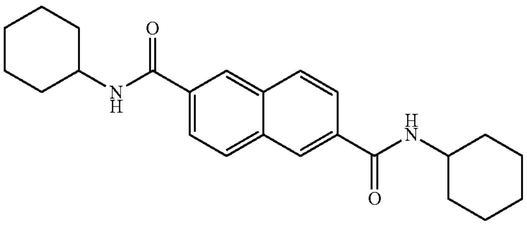

Example 3 Production of the Foams

Polystyrene foams were produced by the process of the invention. This was done using a commercial polystyrene (PS168N, INEOS STYROLUTION, Frankfurt am Main) in the form of 3 mm cylindrical pellets (3×2 mm). For the polystyrene an average molecular weight Mw of 340 000 g/mol was ascertained.

a) Production of the Polymer Powder/Additive Powder Mixtures (Masterbatch)

For this purpose the polymer pellets were first ground using an ultracentrifuge (Retsch ZM200 mill) at a rotary speed of 18 000 rpm with a sieve mesh size of 1000 μm in order to ensure further incorporation and distribution of the additive. During the grinding process, the polymer was cooled with liquid nitrogen.

The ground PS was subsequently provided with 1.0 wt % of the corresponding additive for each powder-powder masterbatch, and was homogenized at 50 rpm with a Heidolph Reax 2 mixer.

b) Batch Foam Process:

Compounding of Polymer-Additive Concentration Series and Injection Molding to Form Specimens Preparation was carried out with a co-rotating twin-screw compounder (DSM Xplore 15 ml). The components were mixed for 5 minutes with a rotary speed of 50 rpm at 260° C. The polymer melt was subsequently left in the injection molding vessel for 2 minutes. Because it is inconvenient to empty the extruder completely and since a defined dead space is left, it is advantageous to prepare a dilution series in order to enable different concentrations. At the start the extruder is filled with 13.5 g of the corresponding material. About 8.1 g can be transferred into the injection molding vessel, while 5.4 g remain in the compounder. With this knowledge it is possible to achieve the desired concentrations.

The following eight concentrations of the above additives in the polymer composition were produced:

1.0; 0.75; 0.5; 0.25; 0.1; 0.05; 0.025 and 0.01 wt %.

Injection molding was carried out using the micro-injection molding machine DSM Xplore 12 mL. The vessel had a temperature of 250° C. and the melt was injected with a pressure of 6 bar for 10 seconds. The pressure was maintained for a further 10 seconds. Round polymer plaques 27 mm in diameter and 1.1 mm in thickness were obtained and tested. In order to eliminate internal stresses in the polymer samples from the injection molding process, they are conditioned at 135° C. for 4 hours in a closed iron mold. The stress-free samples guarantee uniform foaming.

Saturation and Foaming of the Polymer Specimens in the Batch Foam Process

After conditioning, the polymer samples were placed in a BERGHOF HR-500 high-pressure autoclave and saturated with 50 bar of $CO_2$ at room temperature for 24 hours.

After the removal of pressure, the samples were left in the air for 18 min in order to achieve a $CO_2$ saturation of around 6.5%. The samples were subsequently immersed for 15 seconds in a hot silicone oil bath at 130° C. in order to induce foaming. In order to stabilize the cells, the resultant foams were cooled first in a cold oil bath and thereafter in a cold water bath for about 20 seconds each. Lastly the resultant foams were washed in soapy water and dried in air for 12 hours prior to further analysis.

c) Foam Extrusion

The foam extrusions were carried out on a tandem extrusion line (Dr. Collin GmbH) (twin-screw extruder with 25 mm screw and L/D 42; single-screw extruder with 45 mm screw and L/D 30), equipped with a slot die having a 0.6 mm slot and 3 mm width.

Extruded pure XPS foam and also a number of XPS foams each with three selected additive concentrations, namely 0.1 and 0.2 and 0.5 wt %, were produced and analyzed. Analogous trials are carried out with SAN foams.

The various additive concentrations in the polymer were obtained by dilution of a masterbatch with pure polymer pellets, using a gravimetric feeder, by monitoring of the flow rates.

A combination of 4 wt % of $CO_2$ and 3 wt % of ethanol was used as (physical) blowing agent. To obtain an XPS reference, PS pellets without carboxamide additive were extruded in the same way.

The relevant process parameters for the foam extrusion are summarized in table 2.

TABLE 2

| Process parameters for the foam extrusion of PS foams | | | | | | |
|---|---|---|---|---|---|---|
| Entry melting temper-ature | Exit melting temper-ature | Die temper-ature | Screw speed | Through-put | Blowing agent [wt %] | |
| [° C.] | [° C.] | [° C.] | [rpm] | [kg/h] | $CO_2$ | EtOH |
| 260 | 106-130 | 123-132 | 8 | 4.5 | 4 | 3 |

Table 3 sets out the results of various extruded foams produced, based on the polystyrene above. The extruded foams differ in the carboxamide additives used (0.1 wt % in each case).

TABLE 3

Mean cell size and foam density of extruded PS foams without additive, with 0.1 or 0.5 wt % Irgaclear XT 386, with 0.1, 0.2 or 0.5 wt % carboxamide 3b

| Additive | Mean cell size and standard deviation (micrometers) | Foam density (kg/$m^3$) |
|---|---|---|
| No additive | 632.1 +/− 183.9 | 52.3 |
| Irgaclear XT 386 (0.1 wt %) | 25.7 +/− 7.8 | 72.6 |
| Irgaclear XT 386 (0.5 wt %) | 31.3 +/− 10.1 | — |
| Bisamide (3b) (0.1 wt %) | 14.4 +/− 4.7 | 76.5 |
| Bisamide (3b) (0.2 wt %) | 14.7 +/− 5.5 | 82.8 |
| Bisamide (3b) (0.5 wt %) | 10.7 +/− 4.3 | 71.2 |

The polystyrene foam with carboxamide (3b) shown in table 3 exhibits a small cell size and consequently a significant increase in the cell count even when using 0.1 wt % of the additive. Small-cell, closed-cell foams are obtained.

When 0.2 wt % of carboxylic bisamide (3b) is used in the polystyrene, the mean cell size of the foam is 14.7 and the foam density is 82.8 kg/$m^3$. When 0.5 wt % of carboxylic bisamide (3b) is used in the polystyrene, the mean cell size of the foam is 10.7 micrometers and the foam density is 71.2 kg/$m^3$.

With the other bisamide derivatives (1a-d), (2a-d) and (3a, c-d) of the invention as well, in the batch foam process at the tested concentrations (0.1; 0.25; 0.5 wt % of the bisamide) in polystyrene, small-cell and closed-cell foams were obtained in each case, and also have a very largely homogeneous cell size.

When the known trisamide derivative Irgaclear XT 386 was used in the batch foam process, conversely, at the tested concentrations (0.1; 0.25; 0.5 wt % of the trisamide) in polystyrene, the foams obtained in each case had much larger cells, which also did not have a homogeneous cell size.

In the foam extrusion process, using 0.1 wt % of Irgaclear XT 386 in the polystyrene, the mean cell size of the foam was 25.7+/−7.8 micrometers, and when using 0.5 wt % in the polystyrene the mean cell size of the foam was 31.3 micrometers.

Extensive analyses of the thermal conductivity of the XPS foams were also carried out (on round plaques 60 mm in diameter). It was found that the bisamides of the formula (I), even used at a low concentration in the polymer, lead to much better insulation properties (e.g., at 0.1 wt % of the bisamide 3b in the above polystyrene of +7%) in the foams than in the case of corresponding foams produced with the trisamide additive Irgaclear XT 386 in polystyrene.

In further analyses with the batch foam process it emerged that the additives of the invention can also be used advantageously in other polymers. Hence with the bisamide derivative (such as 3b, for example) it was possible, even using 0.1 wt %, to achieve a significant reduction in the mean cell size in a styrene-acrylonitrile copolymer (Luran® 25100, INEOS Styrolution).

The polymer foam obtained with carbon dioxide (130° C., 25 seconds) had a mean cell diameter of the foam of 16.4+/−6.1 micrometers and the foam density was 39.9 kg/$m^3$. A significant increase in the cell count was found, and a small-cell, closed-cell SAN foam was obtained. The cell size distribution was homogeneous as well.

The compounds of the formula (I) therefore enable the provision of new closed-cell foam products which can be employed advantageous even in composite elements (having two or more layers).

The invention claimed is:

1. A process for producing a foam from at least one styrene polymer component (S) and at least one additive of the general formula (I), comprising the steps of:

a. heating at least one styrene polymer component (S) to give a melted polymeric molding compound,
b. introducing a blowing agent (T) into the melted polymeric molding compound, to form a foamable composition (Z), and
c. foaming the foamable composition (Z) to give a foamed molding, wherein at least one carboxylic bisamide of the general formula (I) is used in the melted polymeric molding compound, (I)

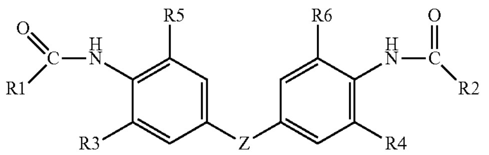

wherein:

Z is a $C_1$-$C_5$ alkylene group or an oxygen atom or a sulfur atom;

$R_1$ and $R_2$ independently of one another are a branched $C_3$-$C_{12}$ alkyl radical or unbranched $C_1$-$C_{12}$ alkyl radical, a $C_3$-$C_{12}$ cycloalkyl radical, or a benzyl radical; and $R_3$, $R_4$, $R_5$, and $R_6$ each independently of one another are hydrogen, an unbranched $C_1$-$C_6$ alkyl radical, or a branched $C_3$-$C_6$ alkyl radical.

2. The process of claim 1, wherein in the general formula (I) $R_1$ and $R_2$ independently of one another are a $C_3$-$C_{12}$ cycloalkyl radical.

3. The process of claim 2, wherein in the general formula (I) $R_1$ and $R_2$ independently of one another are a cyclohexyl radical, a cyclopentyl radical, a butyl radical, or a benzyl radical.

4. The process of claim 1, wherein in the general formula (I) Z is a methylene group and $R_3$, $R_4$, $R_5$, and $R_6$ each independently of one another are a $C_1$-$C_6$ alkyl radical.

5. The process of claim 1, wherein the carboxylic bisamide of the general formula (I) is used in an amount of 0.01 to 2.0 wt %, based on the total weight of the melted polymeric molding compound.

6. The process of claim 1, wherein the blowing agent (T) selected from the group consisting of pentane, cyclopentane, carbon dioxide, ethanol, and a mixture thereof is introduced into the melted polymeric molding compound.

7. The process of claim 1, wherein the styrene polymer component (S) used is a polystyrene (PS) and/or a copolymer containing styrene and acrylonitrile.

8. The process of claim 7, wherein the styrene polymer component (S) used is styrene-acrylonitrile (SAN).

* * * * *